(12) United States Patent
Zimmerman et al.

(10) Patent No.: US 6,446,512 B2
(45) Date of Patent: *Sep. 10, 2002

(54) METHOD OF DETERMINING THE TYPE OF FLUID FLOW PROBE INSERTED INTO A FLOW METER

(75) Inventors: Douglas J. Zimmerman, Fridley; Richard J. O'Brien, Prior Lake; Lloyd E. Graupman, Plato, all of MN (US)

(73) Assignee: Medtronic Avecore Cardiovascular, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/265,751

(22) Filed: Mar. 10, 1999

Related U.S. Application Data

(60) Provisional application No. 60/077,925, filed on Mar. 13, 1998.

(51) Int. Cl.[7] ................................................. G01F 1/58
(52) U.S. Cl. ................................. 73/861.12; 73/861.11; 600/504
(58) Field of Search ........................ 73/861.12, 861.08, 73/861.15, 861.16, 861.13, 861.14, 861.17, 861.11, 866.5

(56) References Cited

U.S. PATENT DOCUMENTS

| | | | | |
|---|---|---|---|---|
| 4,195,515 A | | 4/1980 | Smoll | 73/194 |
| 4,346,604 A | | 8/1982 | Snook et al. | 73/861 |
| 4,358,964 A | | 11/1982 | Otsuka | 73/861.13 |
| 4,800,757 A | * | 1/1989 | Hashinoki et al. | 73/597 |
| 4,881,413 A | | 11/1989 | Georgi et al. | 73/861.12 |
| 5,220,841 A | | 6/1993 | Brown et al. | 73/861.12 |
| 5,325,728 A | | 7/1994 | Zimmerman et al. | 73/861.12 |
| 5,398,552 A | | 3/1995 | Marsh | 73/861.12 |
| 5,417,119 A | | 5/1995 | Smoll | 73/861.12 |
| 5,450,758 A | | 9/1995 | Smoll | 73/861.15 |
| 5,564,108 A | * | 10/1996 | Hunsaker et al. | 395/800 |
| 5,657,761 A | * | 8/1997 | Okada et al. | 128/660.01 |
| 5,659,392 A | * | 8/1997 | Marcus et al. | 356/357 |
| 5,685,301 A | * | 11/1997 | Klomhaus | 128/633 |

\* cited by examiner

*Primary Examiner*—Harshad Patel
(74) *Attorney, Agent, or Firm*—Thomas G. Berry; Harold R. Patton; Daniel W. Latham

(57) ABSTRACT

An inline electromagnetic flow probe, and its corresponding flow transducer, incorporate mutually compatible features that permit a single transducer to identify which of a plurality of types of flow probes has been inserted into the transducer.

7 Claims, 3 Drawing Sheets

METHOD OF DETERMINING THE TYPE OF FLUID FLOW PROBE INSERTED INTO A FLOW METER

CROSS-REFERENCE TO RELATED APPLICATION

This application claims the benefit of provisional application number 60/077,925 filed Mar. 13, 1998.

TECHNICAL FIELD

This invention concerns the determination of characteristics for inline electromagnetic fluid flow probes and transducers.

BACKGROUND

Inline electromagnetic fluid flow probes and transducers are commonly used for non-invasive measurement of fluid flow.

SUMMARY OF THE INVENTION

The invention is a method and apparatus for determination of characteristics of inline electromagnetic fluid flow probes and transducers. The ability to determine such a characteristic enables one to design a system in which a single flow meter may be used with a plurality of probes of differing characteristic; by incorporating the invention into the flow meter, it may determine what type of flow probe has been associated with the flow meter, and automatically adjust its operation accordingly. The scope of the invention encompasses the set of flow probes themselves, as well as the combination of the flow probes and the transducer which is designed to determine the characteristic of each flow probe.

DETAILED DESCRIPTION

Figure 1:
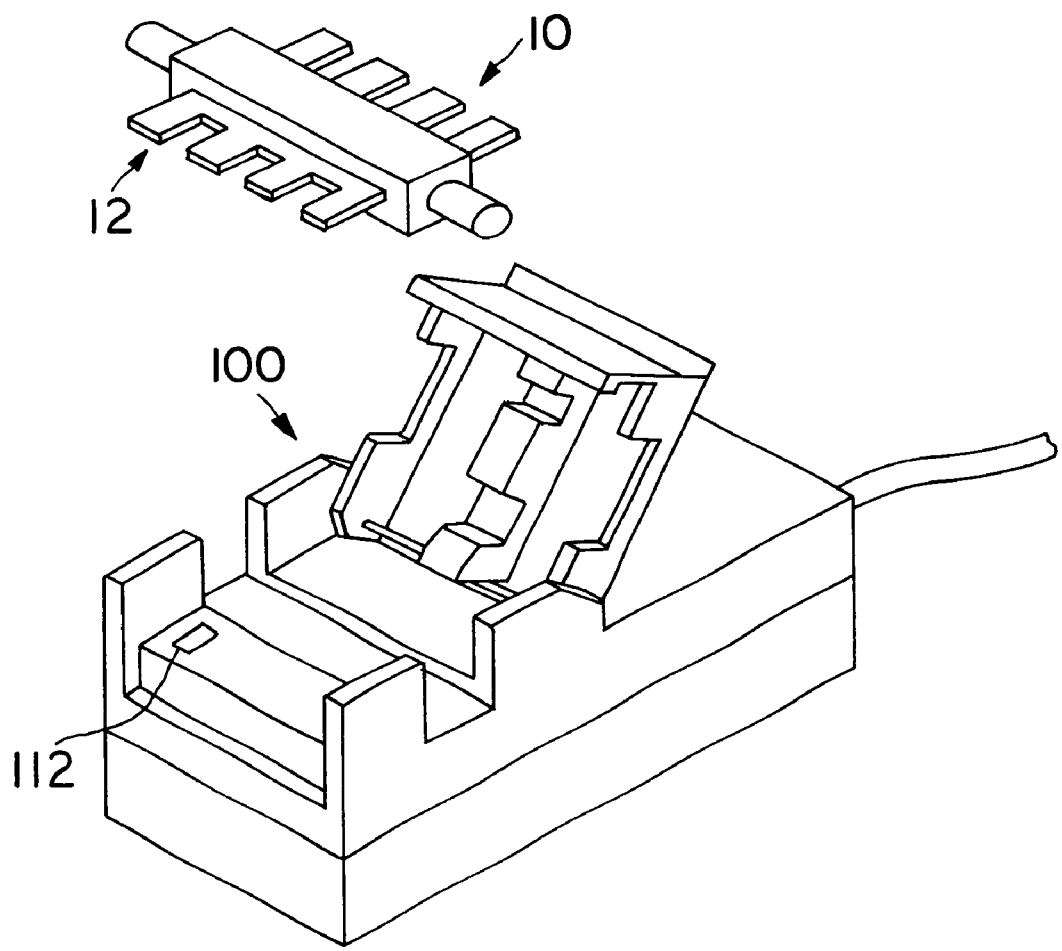
FIG. 1 is a perspective exploded view of an electromagnetic flow probe and transducer of this invention.

FIG. 1 shows a perspective view of an inventive electromagnetic flow probe 10 and associated flow transducer 100. Except as described below, the probe 10 and transducer 100 correspond to the insert and flow meter, respectively, taught in U.S. Pat. No. 5,325,728 (Zimmerman, et al.), which is incorporated by reference. The principles of the invention can be embodied into the flow detection systems taught in any of the following, all of which are also incorporated by reference into the specification and drawings of this application: U.S. Pat. No. 4,881,413 (Georgi et al.), U.S. Pat. No. (5,417,119) (Smoll); U.S. Pat. No. 4,195,515 (Smoll); U.S. Pat. No. 4,358,964 (Otsuka et al.); U.S. Pat. No. 4,346,604 (Snook et al.); and U.S. Pat. No. 5,450,758 (Smoll).

Flow measurement systems of the types disclosed in the documents noted above are commonly used in commercial cardiac perfusion systems to permit the non-invasive measurement of blood flow. For example, for an adult patient, the Medtronic Bio-Medicus Model 550 BioConsole and BP-80 Bio-Pump centrifugal pump are designed to be used with the Medtronic Model DP38 flow insert and FS50 flow transducer; similarly, for a pediatric patient, the Model 550 BioConsole and BP-50 Bio-Pump centrifugal pump are designed to be used with the Medtronic Model DP38P flow insert and FS50P flow transducer. The pediatric models are generally identical to the adult models with the exception changes dictated by the reduced blood volume of the pediatric patient. Labeling and mechanical features distinguish the two types (sizes) of flow inserts and transducers.

The probe 10 and transducer 100 of this invention permit a single model of transducer to support multiple models of probes, including the specific features of automatic recognition of probe type; automatic identification of probe type to the equipment operator; automatic logging of probe type into any suitable form of electronic data storage, to permit historical logging and analysis of flow probe use (e.g., a histogram of the number of each type of flow probe used with the transducer, or of the total flow time of each such type); and automatic configuration of the transducer to reflect parameters (e.g., transducer gain) specific to the type of probe employed. The preferred parameter for probe type is patient type, i.e., adult or pediatric, but the invention includes any suitable parameter, and the invention is specifically not limited to parameters presenting only two possible values (not including the third, or "null" value, which is no flow probe present at all).

To accomplish these features, flow probe 10 includes a feature from which the transducer 100 can discern the type of flow probe. In general, any non-ferrous feature which can be sensed by the transducer is possible; ferrous features would require electromagnetic sensing that would interfere with the electromagnetic principles upon which fluid flow is measured. The preferred class of non-ferrous features is that of optical features. Any optical feature which indicates a difference between otherwise identical flow probes is acceptable. Examples include (but are not limited to) reflectivity, color, modulation, or phase shift. Optical symbol recognition (including optical character recognition) can also be used.

The preferred feature is a reflective surface, and even more preferred features are retroreflective surfaces and materials such as partially silvered spheres, the common cube-corner retroreflector, and variations of those designs. The reflective feature may be incorporated into the flow probe by adhering to the flow probe a separate material which bears the reflective surface itself. Or, the reflective feature may be physically embedded into the flow probe material by molding, chemical etching, laser cutting, or any other suitable surface treatment method whether chemical, mechanical, or electrical in nature. And, as known in the retroreflector art, a particular surface of a transparent material can be rendered retroreflective by incorporating retroreflective features into the side of the material opposite that which the light first strikes.

In any embodiment of the invention which uses an optically-based feature, the wavelength can be in the infrared, visible, or ultraviolet regions of the spectrum. The visible region is preferred because inexpensive and safe components for emission and detection are available. For example, the emitter can be a red light emitting diode available from the Hewlett-Packard Company as part number HLMP-6000-010.

Similarly, the feature can be a mechanical or structural feature which mates with, or is otherwise detectable by, the detector included in the transducer. Mechanical features are not preferred if backward compatibility with the large population of existing transducers is desired. However, if backward compatibility is not an issue, mechanical features are fully within the scope of the invention.

Referring again to FIG. 1, flow probe 10 includes at least one feature 12 (indicated as being on the underneath side of flow probe 10). Feature 12 complements detector 112 included in transducer 100. When flow probe 10 is properly placed in transducer 100, detector 112 detects presence or absence of feature 12 (or, alternatively, it "reads" a value corresponding to the specific feature present). Detector 112 then signals the flow transducer as appropriate to identify the type of flow probe present. In this as well as all embodiments of the invention, the number of features 12 is preferably greater than one even though all such features represent the same indication of flow probe type. Multiple redundant features can provide multiple redundant measurements, and therefore safeguards against false detection.

Figure 2:
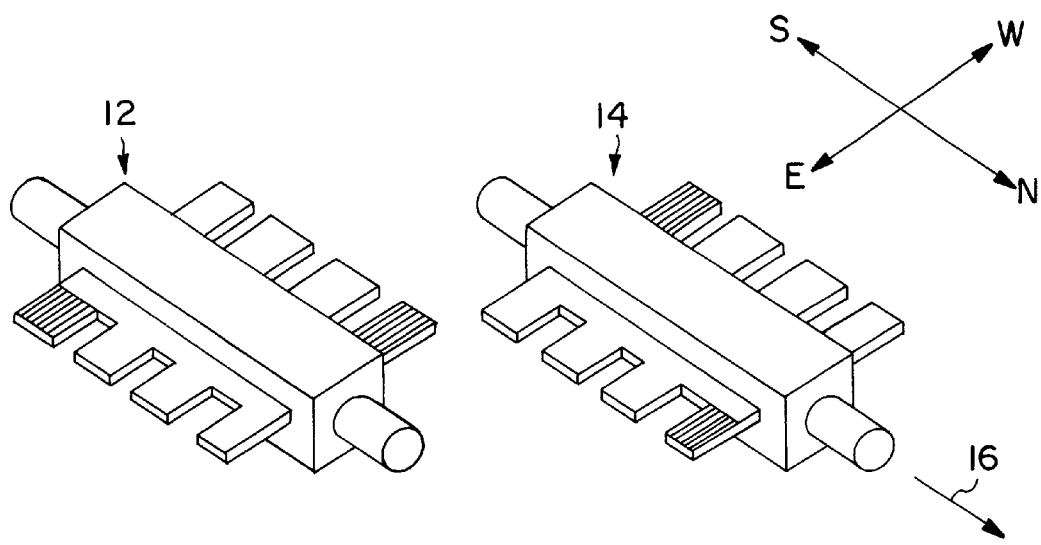
FIGS. 2 and 3 are perspective views of two embodiments of a set of electromagnetic flow probes of this invention.
Figure 3:
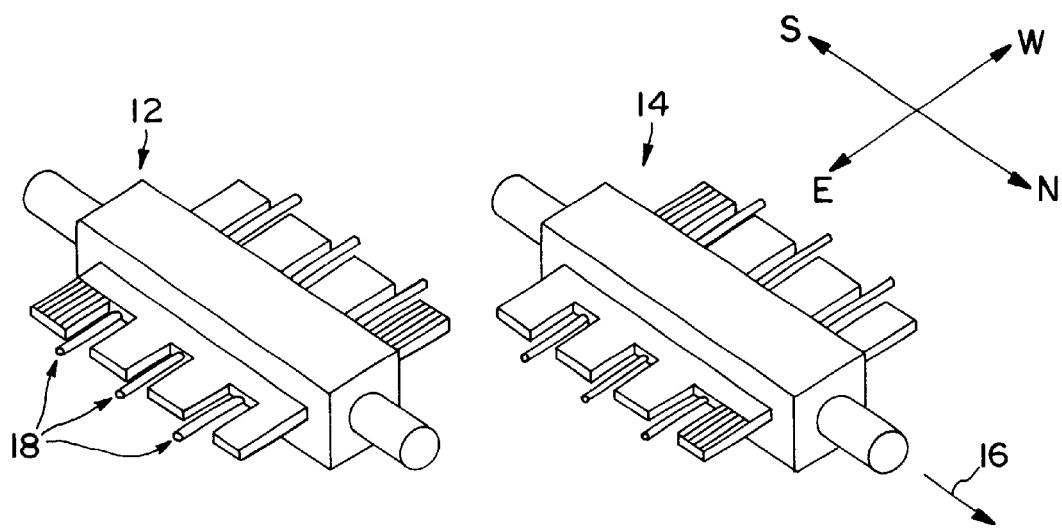

FIGS. 2 and 3 each illustrate embodiments of the invention that are suitable for incorporation into systems based on the Medtronic Bio-Medicus Models DP38/38P (adult/pediatric) flow inserts and FS50/50P (adult/pediatric) flow transducers, except as described below. In each embodiment, the preferred parameter indicated by the feature is the adult or pediatric identification of the flow probe. At a minimum, the detector signals the transducer to record the type of probe inserted, and therefore to adjust the signal gain to reflect the different fluid volume passing through the flow probe.

Each of FIGS. 2 and 3 illustrate the flow probe 120 of FIG. 2 as compared to a physically compatible but functionally incompatible flow probe 140. Flow probe 120 incorporates features 12 on its northwest and southeast corners, taking the flow direction axis 16 as north. Flow probe 140 incorporates features 12 on its northeast and southwest corners, again taking the flow direction axis 16 as north. Thus, the two flow probes present mutually incompatible feature profiles to the set of detectors within the transducer 100. The probes shown in FIGS. 2 and 3 each require insertion into the transducer such that the features are directed toward the detectors; this produces a flow probe with distinguishable "up" (working) and "down" (null value) sides. The "up" side is shown in FIG. 3. An even more preferred embodiment would have four redundant features on each probe, so that the probe could be inserted into the transducer in any orientation. In this embodiment, flow probe 120 incorporates features on its upper northwest, upper southeast, lower northeast, and lower southwest corners, again taking the flow direction axis 16 as north and the side seen in the Figure as up. In the same convention, flow probe 140 incorporates features on its upper northeast, upper southwest, lower northwest, and lower southeast corners. Use of these embodiments of flow probes requires that the transducer have four detectors, one at each of the northwest, northeast, southwest, and southeast corners. The set of four detectors can be on either the upper or lower portion of the transducer and still be able to fully discriminate between the two types of flow probes using both of two redundant detectors for each type, and mutually exclusive sets of two such detectors.

FIG. 3 illustrates an embodiment of the invention which is even more preferred than that of FIG. 2. This embodiment includes additional mechanical features 12 designed to prevent the flow probe of this feature from being inserted into existing Medtronic Bio-Medicus Models FS50/50P (adult/pediatric) flow transducers; however, these features would not prevent existing Medtronic Bio-Medicus Models DP38/38P (adult/pediatric) flow inserts from being used with the transducer of FIG. 3. Such "one-way" compatibility (or incompatibility, depending on one's point of view) is desirable in commercial embodiments for quality control, inventory control, and regulatory reasons. Like numbered features are the same as those in FIGS. 1 and 2.

Pins 18 are longer than those used in the existing models of the flow insert, and therefore the pin sensors in the transducer (not shown) are located farther from the centerline of the flow insert. If an existing commercial model of flow probe is inserted into the transducer, the pins of the existing flow probe will not reach the new pin sensors, triggering a "no probe" lockout on the existing transducer. However, the elongated pins 18 of the new embodiment will still engage the pin sensors on the existing transducer design. The existing transducer cannot determine the flow probe type using feature 12, so the selection of the proper type of probe (and associated adjustment of the transducer) must be done manually as is the case currently.

Figure 4:
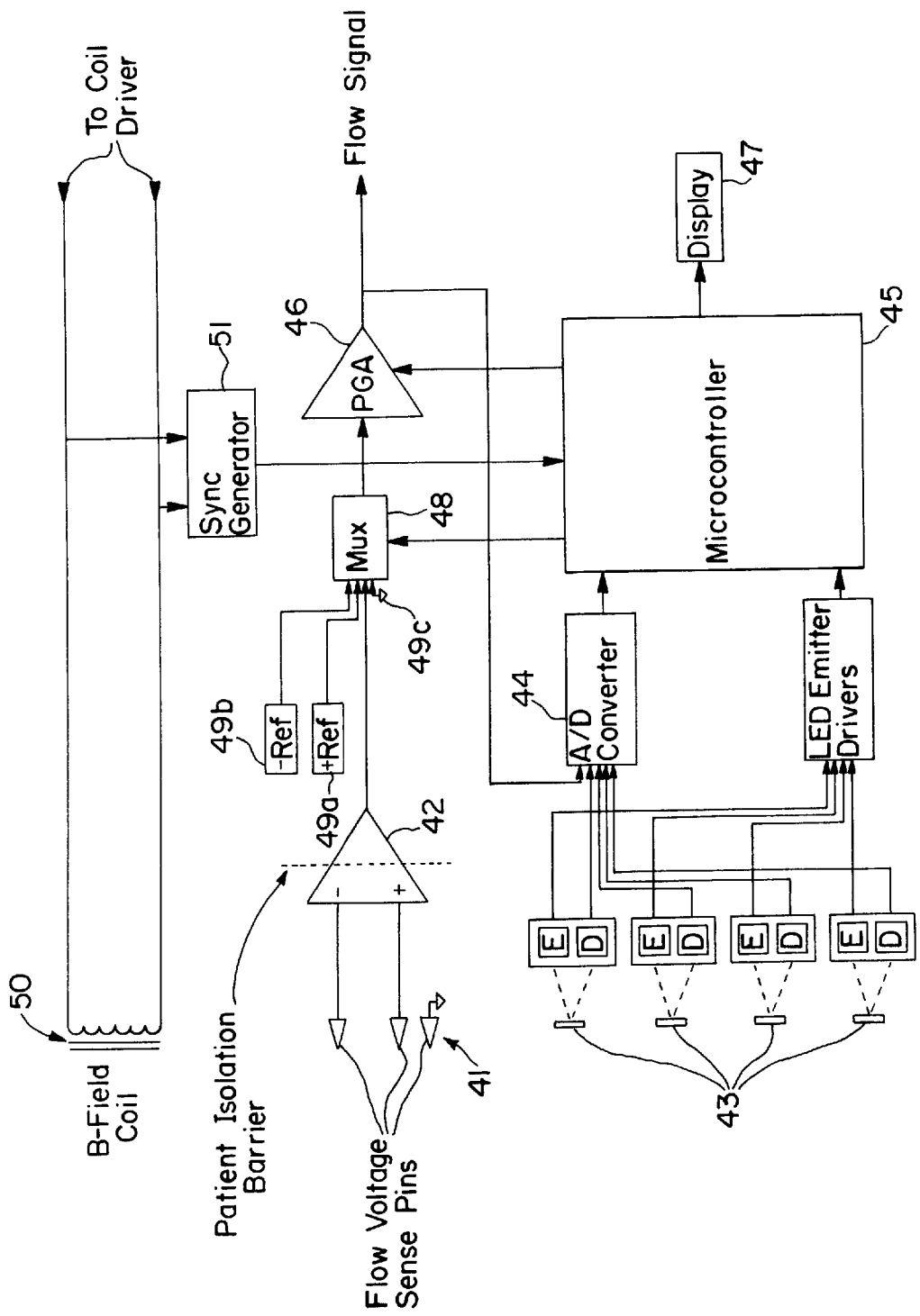
FIG. 4 is an electronic schematic of a preferred microcontroller architecture for the transducer of this invention.

FIG. 4 is an electronic schematic illustrating the use of the embodiment of FIG. 3 in a preferred microcontroller architecture. (Functionally equivalent analog components and/or techniques can be substituted for any or all of the functional components shown.) This architecture is specifically adapted for use with the Medtronic Bio-Medicus Bio-Pump centrifugal blood pump (not shown).

Signals from the pin sensors 41 provide a flow signal through an isolated gain stage amplifier 42 incorporated into the transducer. This buffers the low-level signals and provides a galvanic isolation barrier from the patient.

Outputs from each of one or more detectors 43 are inputs to an analog/digital converter 44 coupled to a microcontroller 45. The microcontroller program acquires ambient light readings from each detector 43 when no probe is present. When a probe is present, the microcontroller 45 cycles through all of the detectors and uses the difference between those values and the ambient light values to determine reflectance.

A suitable algorithm in the microcontroller 45 determines flow probe type. Once the microcontroller 45 has done so, it appropriately configures a programmable gain amplifier (PGA) 46. If present, the optional operator display 47 shows the detected flow type from the choices of error condition (no flow probe present or no unambiguous type of flow probe detected), adult type present, and pediatric type present.

In a preferred but not required embodiment, potential hazards that might occur due to failures within the PGA 46 are addressed by the Built-In-Self-Test (BIST) circuitry. This consists of a multiplexer 48 connected to three voltage sources. The positive and negative reference voltages 49a and 49b verify operation of the PGA 46 at signals above and below ground, below ground, respectively; the ground reference source 49c verifies PGA performance and also replaces the flow signal if no flow probe is detected.

A magnetic (B-field) drive coil 50 rotates the pump (not shown) through a non-contact magnetic coupling, thus controlling pump speed and therefore blood flow. The drive signal for the drive coil also drives a generator 51 to synchronize the microcontroller with the flow signal. This ensures that BIST testing is performed outside the flow sample window. Thus, flow transducers incorporating the invention can be used in existing transducers without modification.

To support new transducers where it may be desirable to indicate the insert type of the console and yet still provide compatibility with existing consoles, the BIST sequence is modified in accordance with the flow probe type. This embodiment extracts the BIST signal modulation on the flow signal to determine flow transducer status.

We claim:

1. A method of determining whether a first or a second type of inline electromagnetic flow probe is inserted into a flow meter comprising the steps of:

provide a flow probe having one of a first probe feature characteristic of the first type of flow probe or a second probe feature characteristic of the second type of flow probe;

providing a flow meter having means for sensing the first probe feature and the second probe feature, the flow meter outputting a first type of signal upon sensing the first probe feature and a second type of signal upon sensing the second probe feature;

inserting a flow probe into the flow meter, the flow probe having one of the first probe feature or the second probe feature;

outputting a signal from the flow meter responsive to inserting the flow probe, the signal being one of the first type of signal or the second type of signal, whereby the first type of signal indicates the insertion of the first type of flow probe and the second type of signal indicates the insertion of the second type of flow probe.

2. The method according to claim 1 further comprising the step of coupling the flow meter to a means for sensing the signal outputted by the flow meter.

3. The method according to claim 1 or 2 wherein the step of providing the flow meter further comprises providing a flow meter having means for optically sensing the first probe feature and the second probe feature.

4. The method according to claim 3 wherein the means for optically sensing the first probe feature and the second probe feature comprises means for sensing an optical feature selected from the group consisting of reflectivity, color, modulation, phase shift, or optically recognizable symbols.

5. The method according to claim 4 wherein the optical feature is optical retroreflectivity.

6. The means according to claim 4 wherein the means for optically sensing comprises means for sensing an optical feature by infrared, visible or ultraviolet light.

7. The method according to claim 1 wherein the step of providing the flow meter further comprises providing a flow meter having a flow probe cavity, the cavity adapted to mechanically accept the insertion of the flow probe.

* * * * *